United States Patent [19]

Keller

[11] Patent Number: 5,137,535
[45] Date of Patent: Aug. 11, 1992

[54] ENDOPROSTHESIS WITH COMPLEMENTARY CONE CONNECTION AND ECCENTRIC SECURING SCREW

[75] Inventor: Arnold Keller, Kayhude, Fed. Rep. of Germany

[73] Assignee: Waldemar Link GmbH & Co., Hamburg, Fed. Rep. of Germany

[21] Appl. No.: 755,695

[22] Filed: Sep. 6, 1991

[30] Foreign Application Priority Data

Sep. 7, 1990 [DE] Fed. Rep. of Germany ....... 4028510

[51] Int. Cl.⁵ .......................... A61F 2/38; A61F 2/30; A61F 2/36
[52] U.S. Cl. ...................... 623/20; 623/18; 623/23
[58] Field of Search ........... 623/16, 18, 19-23

[56] References Cited

U.S. PATENT DOCUMENTS

| 3,102,536 | 9/1963 | Rose | 623/23 |
| 4,198,711 | 4/1980 | Zeibig | 623/23 |
| 4,676,797 | 6/1987 | Anapliotis et al. | 623/23 X |
| 4,705,520 | 11/1987 | Ahrens | 623/23 |

FOREIGN PATENT DOCUMENTS

| 0000549 | 2/1979 | European Pat. Off. | 623/18 |
| 1594365 | 6/1970 | France . | |
| 2222889 | 10/1974 | France . | |
| 660955 | 8/1983 | Switzerland . | |
| 1130324 | 12/1984 | U.S.S.R. | 623/22 |

OTHER PUBLICATIONS

Search Report for EP 91 11 3877

Primary Examiner—Ronald Frinks
Attorney, Agent, or Firm—Chilton, Alix & Van Kirk

[57] ABSTRACT

In an endoprosthesis with two or more individual parts (1, 2), of which one has a cone part (2) with a conical bore (4) and of which another has a cone part (1) with a complementary conical projection (3), the parts (1, 2) being connected by inserting the conical projection (3) into the conical bore (4), a particularly firm connection is achieved by virtue of the fact that a securing screw (6) is provided in the area of the cone connection (3, 4). The securing or fastening screw (6) advantageously cooperates eccentrically with the corresponding recess in the other part, in order to prestress the cone connection for the purpose of a still firmer connection.

18 Claims, 4 Drawing Sheets

ENDOPROSTHESIS WITH COMPLEMENTARY CONE CONNECTION AND ECCENTRIC SECURING SCREW

BACKGROUND AND SUMMARY OF THE INVENTION

The invention relates to an endoprosthesis with two or more individual parts, of which one has a cone part with a conical bore and of which another has a cone part with a complementary conical projection, the parts being connected by inserting the conical projection into the conical bore, and there being provided, in the area of the cone connection, a securing screw whose axis is perpendicular to the cone axis and which is screwed into one of the cone parts and with its front end engaged in a recess in the other cone part.

Endoprostheses often consist of two or more individual parts which can then be joined together as required, for example a prosthesis main part and a prosthesis head. Such multi-part prostheses have the advantage that, with relatively few individual parts, a great many combinations between prosthesis head and prosthesis main part can be produced, so that the number of parts to be kept in store is lower.

The prosthesis is made up from the two individual parts by means of the part with the conical bore being placed on the part with the conical projection and driven home. This provides a generally reliable and permanent connection, as is necessary.

It is known to secure a connection of this type, which is already inherently firm, by means of an additional securing screw (EP 0,000,549 A1).

The aim of the invention is to provide an endoprosthesis of the type mentioned at the outset, in which the two parts can be connected permanently to one another even more reliably.

The solution according to the invention consists in the front end of the securing screw being tapered and cooperating eccentrically with the recess.

By means of the eccentric cooperation, the securing screw not only secures the connection, but exerts an additional force in the direction in which the cone connection is pressed together still further. Such an eccentrically acting cone screw is known from shelf construction (FR-B-2,222,889). Apart from the fact that shelf construction can provide no stimulus for the constructor of an endoprosthesis, the cone screw there has the purpose of drawing together two parts which can be displaced one inside the other, the connection falling apart without the cone screw. In the invention, the cone connection is in itself already a reliable and firm connection, whose reliability, however, is still further increased by the arrangement of the cone screw according to the invention.

Such securing screws are normally only used in cases where the two parts would not cling to one another reliably without such screws, for example if a cylindrical bore is placed on a cylindrical support. It is the contribution of the invention to have recognized that by using a securing screw, even though the latter does not appear to be absolutely necessary in a cone connection, an even more secure attachment can be obtained.

In an advantageous embodiment, the securing screw is arranged in the outer cone part and cooperates with a bore or an annular groove in the inner cone part.

An essential feature is that the front end of the securing screw cooperates with the recess eccentrically or axially offset. If, in this case, the securing screw is arranged in the outer cone part, then the front end of the securing screw should cooperate with the recess eccentrically or axially offset to the side of the screw axis which is directed towards the tapering end. Thus, according to the invention, the securing screw contacts the outer end of one of the recess side walls with a greater force than the force exerted on the outer end of the other side wall. For example, in one embodiment, the screw contacts the outer end of the recess side wall that is closer to the narrow end of the cone parts, and does not contact the end of the recess side wall that is further from the narrow end.

In the eccentric arrangement of the invention, the securing screw not only fixes the position previously obtained by striking the parts together, but also exerts on one side a force by means of which the two cone parts are pressed together or tensioned still further. In this way, for example, tolerances can be compensated. Even in the case of very accurately machined cone parts, it is possible that the securing screw and recess will not match each other absolutely concentrically, since a small variation in dimension can lead to a greater displacement on account of the normally relatively slight slope of the cone or a normally very small cone angle in the axial direction. Such tolerances can be compensated by the eccentric arrangement. In addition, if the cone connection was made insufficiently secure by mistake, or if, as a result of aging process, the cone connection threatens to come loose, the securing screw does not prevent a renewed, firmer pressing together of the cone parts by means of external loads, since the securing screw or securing screws do not exert any force in this direction, but instead permit a movement. Thus, in the unfavorable conditions mentioned, this embodiment prevents the cone screw from having exactly the opposite effect, namely that of preventing a more secure connection.

A further advantage of this embodiment lies in the fact that the securing screw does not prevent the sintering together of the cone connection, but instead, as a result of the axially offset arrangement of the securing screw with respect to the recess, activation of the securing screw effects an even firmer pressing together of the cone connection in the longitudinal direction.

In another advantageous embodiment, the securing screw is arranged in a bore of the inner cone part provided with a thread, and cooperates with a bore or with a slot extending over a part of the periphery. The screw can in this case be turned from the outside by means of a tool, which is pushed through the outer cone part, the bore in the inner cone part being designed as a through-bore, and a counterbore or a corresponding slot being provided in the outer cone part on the radially opposite-lying side of the recess in which the screw is to be engaged. The front end of the screw can be designed to be any suitable shape. Preferably, the screw is tapered, and more preferably it is conical or frustoconical. When the front end is frustoconical, the tool engages on the flat front surface of the truncated cone—the tool thus engages on that end of the screw at which the screw is intended to exert a force on the other cone part. Among other tapered shapes, the front end of the securing screw can have concave or convex sides.

In the embodiment incorporating a securing screw having a frustoconical front end, it is essential that the securing screw cooperates with the recess eccentrically or axially offset, and namely on the side of the screw axis which is directed away from the tapering cone end. The particular advantages described above in connection with the eccentric arrangement are then once again obtained.

If the walls of the recess, with which the securing screw cooperates, are bevelled at least in the parts pointing towards the securing screw, there is no punctiform contact here, which contact could under certain circumstances lead to a deformation of the screw or the walls. Greater forces can therefore be transmitted. In this respect, the angle of the bevelling should correspond as closely as possible to the corresponding angle of the front end of the securing screw.

Instead of screwing a single securing screw into the corresponding bore provided with a thread, it is also possible here, after tightening the screw, to screw in and tighten a counterscrew.

Although in most cases one securing screw is sufficient, it is also possible to provide more than one securing screw. The two securing screws can in this case act on opposite-lying sides of the cone, for example. In order to reliably prevent the loosening of the securing screw or screws, a counterscrew can be screwed in behind the securing screw or screws.

The securing screw is positioned generally perpendicular to the axis of the conical bore and/or conical projection, i.e. the axis of the securing screw is $90° \pm 20°$ from the axis of the conical bore and/or conical projection. It is further noted that the conical bore and conical projection can be replaced by complementary bores and projections having other tapered shapes which result in a substantially equivalent type of connection.

BRIEF DESCRIPTION OF THE DRAWINGS

The invention is described hereinbelow on the basis of advantageous embodiments and with reference to the attached drawings, in which.

DETAILED DESCRIPTION OF THE PREFERRED EMBODIMENTS

Figure 1:
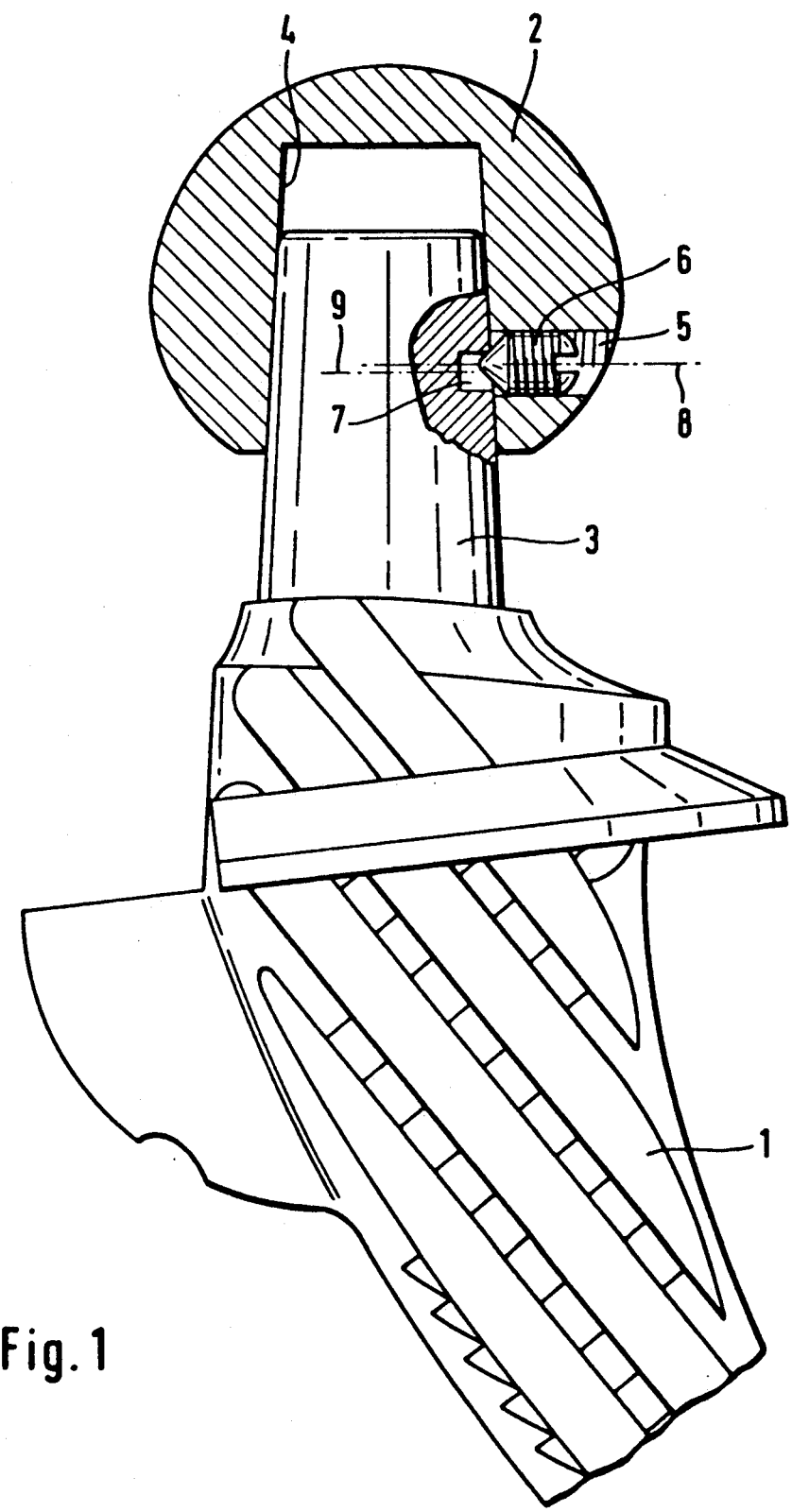
FIG. 1 shows, partially in cross-section, a first embodiment of the invention.

FIG. 1 shows a part of a hip-joint endoprosthesis. On the prosthesis main part, the prosthesis stem 1 which is intended to be inserted in the femur, a prosthesis head 2 is to be attached. For this purpose, the prosthesis main part 1 is provided in the upper part with a conical projection 3, while the prosthesis head 2 has a corresponding conical recess 4. The prosthesis head 2 is provided with a bore 5, which is provided with a thread and into which a securing screw 6 can be screwed, which screw at the front runs out conically to a tip. In the conical projection 3 there is a bore 7, into which the tip of the securing screw can engage, in order to permanently secure the cone connection of the parts 3, 4. As can be seen from the figure, in this embodiment the screw is arranged with its axis 8 eccentric to the mid-line of the axis 9 of the bore 7, so that screw 6 and bore 7 bear against each other only at the outer edge of the recess side wall which is directed towards the tapering end of the cone 3. This provides the particular advantages that the cone connection is tensioned still further but, despite this, does not prevent a further pushing together of the parts.

Figure 2:
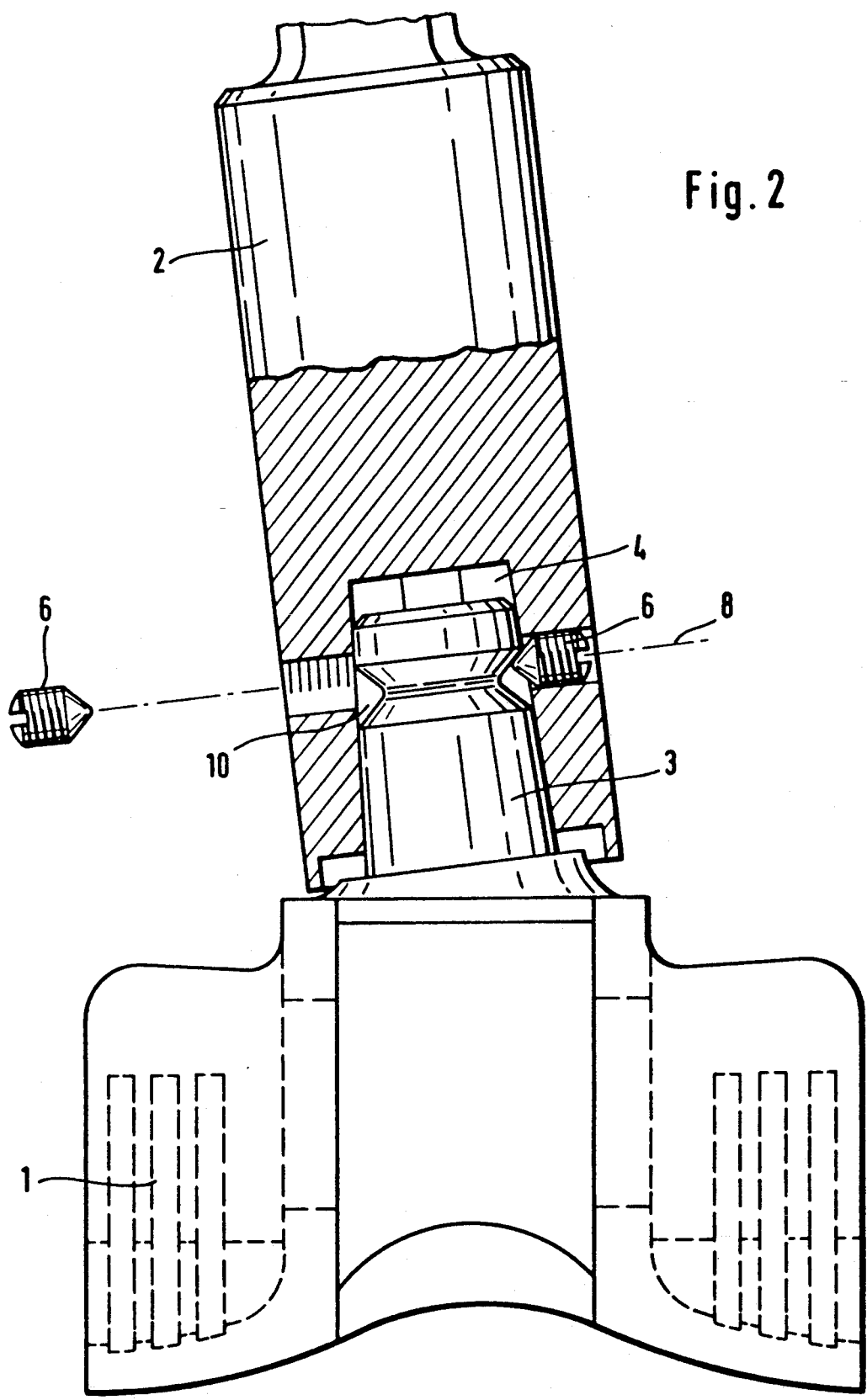
FIG. 2 shows, partially in cross-section, a second embodiment.
Figure 3:
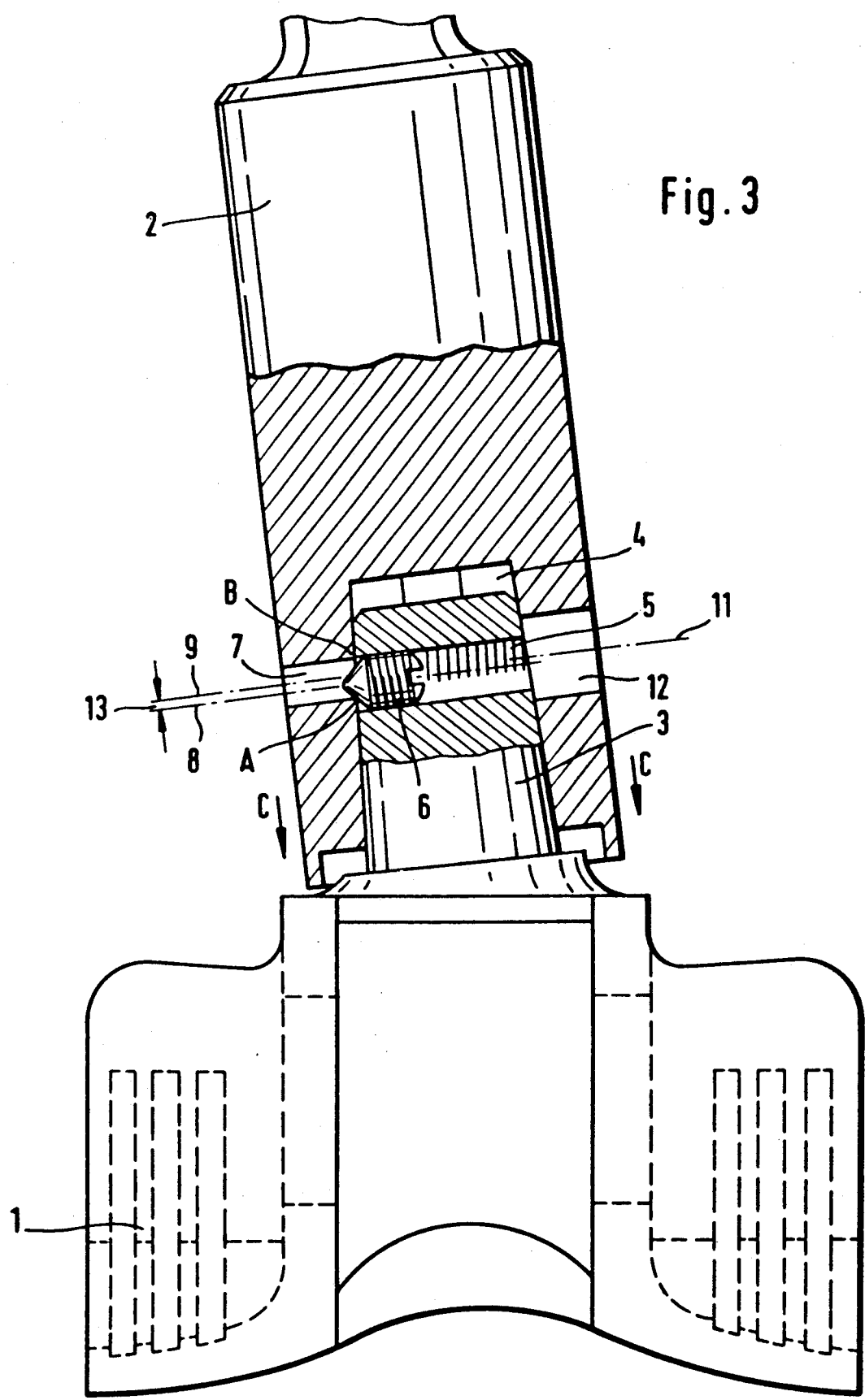
FIG. 3 shows, partially in cross-section, a third embodiment.

In the embodiment in FIGS. 2 and 3, the main part 1 is a knee-joint, on which a prosthesis stem 2 is to be attached. Instead of a bore 7, an annular groove 10 of V-shaped cross-section is provided in the conical projection 3, into which annular groove two screws 6 can engage from two different sides. As can be seen clearly from the figure, the annular groove is again arranged eccentric to the screw axis, so that similar effects are obtained as in the embodiment in FIG. 1. Of course, the annular groove would not have to be symmetrical, since the lower flanks of the groove in the figure do not come into contact at all with the screws 6.

In the embodiment in FIG. 3, the screw 6 is provided in the inner cone part 3. The screw is first screwed back so far inside the threaded bore 5 that it is arranged wholly within the conical projection 3. Then the prosthesis stem 2 is pushed onto the projection 3. A screwdriver can then be applied via a counterbore 12, and the screw 6 in the figure can be screwed towards the left so that it can come into engagement with the bore 7, which lies opposite the bore 12. Here too the axis 8 of the screw 6 is eccentric or axially offset relative to the axis 9 of the bore 7. The corresponding axially offset arrangement is designated by 13. However, the screw 6 must now come to bear on the lower edge of the bore 7 at A, so that the cone part 4 is tensioned securely on the cone part 3 in the direction of the arrows C. At the upper edge at B, the securing screw does not touch the edge of the bore 7, so that a movement of the part 2 in the direction of the arrows C, i.e., an even more secure fitting of the part 2 on the part 1, is not prevented.

In all the embodiments, after the screw 6 has been screwed in, an additional counterscrew (which is not shown in the figures) can be screwed into the bore 5 provided with a thread, in order to fix the connection permanently.

Figure 4:
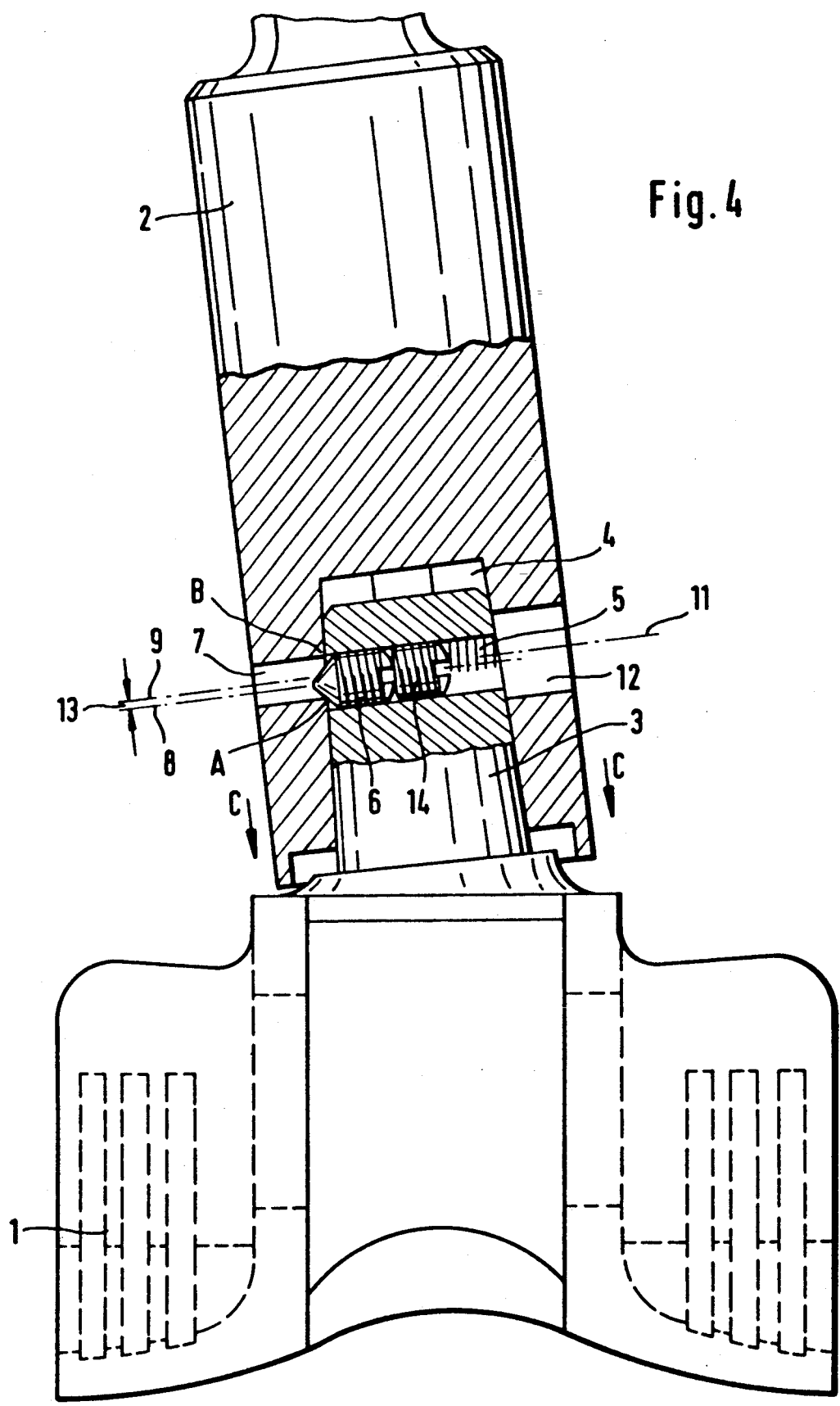
FIG. 4 shows the embodiment in FIG. 3, with an additional counterscrew.

The embodiment in FIG. 4 corresponds essentially to the embodiment in FIG. 3. In addition, a counterscrew 14 also screwed in behind the securing screw 6 in this case, in order to reliably prevent a loosening of the securing screw 6. The counterscrew is in this case arranged behind the securing screw 6, i.e., to the side which is opposite the front end of the securing screw cooperating with the other cone part. Such counterscrews 14 can also be provided in the embodiments in FIGS. 1 and 2, in which case the securing screw 6 must of course be made shorter, or the cone part into which it is screwed must be made thicker, than is shown in the figures.

I claim:

1. An endoprosthesis comprising an outer cone part having an internally tapered conical bore, an inner cone part having a complementary externally tapered conical projection, and a securing screw, the outer and inner cone parts being adapted to be connected by inserting the conical projection into the conical bore, the securing screw being adapted to be screwed into one of the outer cone part and the inner cone part, and having a tapered front end adapted to bear eccentrically against a recess in the other of the outer cone part and the inner cone part.

2. An endoprosthesis according to claim 1, wherein the conical projection and the securing screw each have an axis, the axis of the conical projection being generally perpendicular to the axis of the securing screw.

3. An endoprosthesis according to claim 2, wherein the recess comprises a bore in the inner cone part, and the securing screw is adapted to be arranged in the outer cone part and to bear eccentrically against the bore in the inner cone part.

4. An endoprosthesis according to claim 2, wherein the recess comprises an annular groove in the inner cone part, and the securing screw is adapted to be arranged in the outer cone part and bear eccentrically against the annular groove.

5. An endoprosthesis according to claim 2, wherein the recess has opposed side walls and the front end of the securing screw is adapted to bear eccentrically against a side wall.

6. An endoprosthesis according to claim 5, wherein the conical projection has a wider end and an opposite narrower end, the recess is formed on the inner cone part, and the securing screw is adapted to be arranged in the outer cone part and to bear against the outer end of the recess side wall that is nearer the narrower end of the conical projection.

7. An endoprosthesis according to claim 5, wherein the conical projection has a wider end and an opposite narrower end, the recess is formed in the outer cone part, and the securing screw is adapted to be arranged on the inner cone part and to bear against the outer end of the recess side wall that is nearer the wider end of the conical projection.

8. An endoprosthesis according to claim 5, wherein the side walls of the recess are bevelled, and are bevelled at least in the part directed towards the securing screw.

9. An endoprosthesis according to claim 8, wherein the angle of the bevelling corresponds to the angle of the front end of the securing screw.

10. An endoprosthesis according to claim 1, further comprising a counterscrew for the securing screw.

11. An endoprosthesis according to claim 1, wherein the endoprosthesis has more than one securing screw.

12. An endoprosthesis according to claim 1, further comprising a counterscrew arranged behind the securing screw.

13. An endoprosthesis according to claim 2, wherein the recess comprises a bore in the outer cone part and the securing screw is adapted to be arranged in a threaded bore in the inner cone part and to cooperate with the bore in the outer cone part.

14. An endoprosthesis according to claim 2, wherein the recess comprises a slot in the outer cone part and the securing screw is adapted to be arranged in a slot extending over part of the periphery of the inner cone part.

15. An endoprosthesis according to claim 1, wherein the endoprosthesis is for a hip-joint.

16. An endoprosthesis according to claim 1, wherein the endoprosthesis is for a knee-joint.

17. An endoprosthesis according to claim 1, wherein the securing screw is frustoconical.

18. An endoprosthesis with two or more individual parts, of which one has a cone part with a conical bore and of which another has a cone part with a complementary conical projection, the parts being connected by inserting the conical projection into the conical bore, and there being provided, in the area of the cone connection (3, 4), a securing screw (6) whose axis (8) is essentially perpendicular to the cone axis and which is screwed into one of the cone parts (1, 2) and with its front end engages in a recess (7, 10) in the other cone part (2, 1), characterized in that the front end of the securing screw (6) is conical or frustoconical and cooperates eccentrically with the recess.

* * * * *